United States Patent [19]

Mackool

[11] Patent Number: 5,569,188
[45] Date of Patent: Oct. 29, 1996

[54] APPARATUS FOR CONTROLLING FLUID FLOW THROUGH A SURGICAL INSTRUMENT AND THE TEMPERATURE OF AN ULTRASONIC INSTRUMENT

[76] Inventor: Richard J. Mackool, 31-27 41st St., Astoria, N.Y. 11103

[21] Appl. No.: 419,817

[22] Filed: Apr. 11, 1995

[51] Int. Cl.$^6$ .......................... A61M 31/00; A61M 1/00; A61F 9/00
[52] U.S. Cl. ................................ 604/67; 604/28; 604/31; 604/119; 606/107
[58] Field of Search ................................ 604/28, 30–35, 604/65, 67, 119, 153, 38; 417/326, 477.1; 606/107

[56] References Cited

U.S. PATENT DOCUMENTS

| | | | |
|---|---|---|---|
| 3,693,613 | 9/1972 | Kelman | 128/24 A |
| 4,024,866 | 5/1977 | Wallach | 604/31 |
| 4,038,980 | 8/1977 | Fodor | 128/193 |
| 4,180,074 | 12/1979 | Murry et al. . | |
| 4,493,698 | 1/1985 | Wang et al. | 604/119 X |
| 4,496,342 | 6/1985 | Banko | 604/31 X |
| 4,642,128 | 2/1987 | Solorzano | 55/217 |
| 4,650,461 | 3/1987 | Woods | 604/28 |
| 4,705,500 | 11/1987 | Reimels et al. . | |
| 4,755,168 | 7/1988 | Romanelli et al. | 417/477.1 X |
| 4,798,580 | 1/1989 | DeMeo et al. . | |
| 4,832,685 | 5/1989 | Haines | 604/30 |
| 4,902,276 | 2/1990 | Zakko | 604/28 |
| 5,026,393 | 6/1991 | Mackool . | |
| 5,084,009 | 1/1992 | Mackool . | |
| 5,178,606 | 1/1993 | Ognier et al. | 604/31 |
| 5,209,719 | 5/1993 | Baruch et al. . | |
| 5,286,256 | 2/1994 | Mackool . | |
| 5,354,265 | 10/1994 | Mackool . | |

*Primary Examiner*—Randall L. Green
*Assistant Examiner*—A. T. Nguyen
*Attorney, Agent, or Firm*—Cobrin Gittes & Samuel

[57] ABSTRACT

An apparatus essentially consisting of an aspiration conduit, a pump, and a pressure transducer and logic console which senses vacuum level fluctuations in the aspiration conduit. The aspiration conduit is connected to a surgical cavity. The pump creates a vacuum in the pre-pump aspiration conduit and transports the fluid and/or tissue material from the surgical cavity, through the aspiration conduit and into a collection container. The logic console responds to a predetermined rate of decrease in vacuum in the pre-pump aspiration conduit and causes an electric signal to be sent to 1) the pump, which upon receiving such signal, reverses its action and/or: 2) an electromechanical valve located along the aspiration conduit, which upon receiving such signal acts to occlude the aspiration conduit and terminate the removal of tissue or fluid from the surgical site. The reversal of rotation prevents the occurrence of a fluid surge which would result in the collapse of the surgical cavity. In addition a surgical tool is disconnected from its source of power when the temperature of the surgical tool is above a predetermined value.

15 Claims, 2 Drawing Sheets

APPARATUS FOR CONTROLLING FLUID FLOW THROUGH A SURGICAL INSTRUMENT AND THE TEMPERATURE OF AN ULTRASONIC INSTRUMENT

FIELD AND BACKGROUND OF THE INVENTION

This invention relates to an apparatus which controls the rate of fluid flow through a closed or partially closed hydraulic system. In particular, this invention concerns an apparatus which controls the rate of fluid flow at a surgical site, thus preventing the occurrence of a fluid surge, the sudden increase of vacuum within a surgical cavity and the collapse thereof.

The delicate structures within the surgical cavity, such as an iris, cornea or lens capsule which surround the human lens in the case of the eye, or the walls of the human gallbladder or ureter in cases of stone removal, or the walls of the human arteries in cases of removal of arterial plaque, or the lining of joints in cases of tissue removal therefrom, can experience severe damage from such a collapse.

This invention relates particularly to the field of eye surgery in which material such as a cataract is removed from the eye, and other types of surgery involving the removal of material from within a surgical cavity by the use of fluid flow and aspiration methods. Devices for this purpose exist in the field of eye surgery, as well as surgery involving stone removal from the gallbladder, kidneys, or ureters. Such methods have also been utilized to remove obstructions from arteries.

Ultrasonic or laser and/or mechanical cutting are employed to reduce the unwanted material to a size which may flow uninhibited through the aspiration conduit. However, such material may not always be invariably reduced to an appropriate size, thus resulting in an obstruction in the aspiration conduit.

A fluid surge at the surgical cavity generally occurs pursuant to two events. One such event is when an obstruction, as aforementioned above, is released. The other such event is when trapped air creates uncontrolled aspiration forces within the aspiration conduit.

The sudden release of an obstruction, which may occur at any location in the pre-pump aspiration conduit, results in the occurrence of a fluid surge. As the obstruction impedes fluid flow within the aspiration conduit, the pump employed by the system continues to operate, thereby increasing the vacuum in the pre-pump conduit. Upon release of the obstruction, a fluid surge develops and travels from the surgical cavity into the aspiration conduit. The fluid surge is caused by the aforementioned decrease in vacuum and a rebound of the aspiration conduit which had partially collapsed in response to the vacuum within it.

Other reasons for the occurrence of the fluid surge include the expansion and contraction of air which may at times gain access to the aspiration conduit. A fluid surge may be caused by the sudden contraction of air within the aspiration conduit upon release of an obstruction, when such air had previously expanded during obstruction of the aspiration conduit.

Generally, fluid aspiration devices require the use of a flexible conduit as well as containers to collect the aspirated fluid and/or material. Such devices may also employ mechanisms whereby the flexible conduit may be vented to the atmosphere in order to release accumulated vacuum within the tubing.

The elasticity of the aspiration conduit as well as the air spaces within the container used for collection and/or air introduced into the system during operation may act to create forces which may collapse or expand the conduit and thereby create undesirable, uncontrolled aspiration forces within the system. This can result in periods of undesirable and dangerously increased flow through the aspiration system, with subsequent loss of pressure within the surgical cavity being treated and the collapse thereof.

Various prior art devices have been disclosed for controlling fluid flow and the direction thereof during the removal of material from within the surgical cavity. However, devices employing the automated reversal of a pump, in combination with a pressure transducer and logic system, have not been disclosed.

Mechanisms currently in existence to prevent a fluid surge include intermittent venting of fluid into the aspiration conduit from another source. Such systems require a second source of fluid and shunting valves which may be costly to manufacture and/or more prone to failure than the aspiration system described herein. The apparatus disclosed in this specification is safer, less costly to manufacture, and more efficient than the other fluid control system.

U.S. Pat. No. 4,705,500 to Reimels discloses an aspiration-irrigation system, utilizing a peristaltic pump and a foot operable control unit which controls the speed and rotational direction of the pump. The control unit essentially consists of a foot pedal and a control box.

The rotational direction of the pump is a function of the depression of the pedal. Rotation of the pump counterclockwise creates a negative pressure within the aspiration port, causing aspiration of fluid/tissue particles, while rotation of the pump clockwise creates a positive pressure for ejection of blockage particles.

Although Reimels recites a pump which reverses rotation, it does not disclose or suggest a pressure transducer or a logic system, which senses pressure changes and transmits such information to the pump, which may then automatically reverse its rotation as described in this application. Rather, the operator must manually reverse the rotation of the pump by varying the amount of pressure on the pedal.

U.S. Pat. No. 4,832,685 to Haines discloses an irrigation-aspiration apparatus consisting of an aspiration conduit, a peristaltic pump, and a pressure transducer connected to the aspiration conduit. The pressure transducer generates an electrical signal proportional to the vacuum in the aspiration conduit.

An obstruction in the aspiration is indicated by the vacuum exceeding a pre-set level, whereby the pressure transducer shuts off the pump. The obstruction is ejected from the aspiration conduit by equalizing the pressures in an irrigation conduit and the aspiration conduit, which is accomplished by filing the conduit system with liquid. As soon as the pressure is equalized, the pressure transducer detects the lower level of suction and restarts the pump.

Although Haines recites a peristaltic pump and a pressure transducer, it does not disclose or suggest that the pump reverses rotation upon the vacuum exceeding a predetermined value.

U.S. Pat. No. 4,180,074 to Murry discloses an irrigation-aspiration device comprised of an aspiration tube, a peristaltic pump, a pressure transducer, and a diaphragm. Although Murry recites a peristaltic pump and a pressure transducer, it does not disclose reversal of the peristaltic pump when a blockage of the aspiration tube occurs.

Additionally, U.S. Pat. No. 4,493,698 to Wang discloses a method for controlling the vacuum level in a debris receptacle and aspiration conduit during surgery. Such method primarily consists of an aspiration conduit, a peristaltic pump, a pressure transducer, potentiometers, and a controller.

The system's vacuum is pre-set by the potentiometer, which sends signals of the desired vacuum level to the controller. The controller receives the signal of the actual vacuum in the aspiration conduit from the pressure transducer and adjusts the opening of valves in order to maintain the desired pressure in the aspiration conduit.

Like the aforementioned patens of Murry and Haines, Wang does not disclose or suggest the reversing of the pump'rotation when an occlusion occurs.

U.S. Pat. No. 4,798,580 to DeMeo discloses an irrigation and aspiration system. However, it does not disclose a pressure transducer nor the reversal of the pump when an occlusion in the aspiration conduit occurs.

SUMMARY OF THE INVENTION

The invention's object is to overcome the disadvantages in the prior art devices by providing an improved fluid control apparatus for use during surgery. More specifically, the invention's object is to prevent a fluid surge from occurring during aspiration from a surgical cavity which would result in the collapse of the cavity. This is accomplished by occluding the aspiration conduit and/or reversing the flow at some portion of the aspiration system.

The invention embodies an aspiration conduit, which may extend from a surgical handpiece into a collection container, and a pump, which reverses rotation upon receiving an electric signal from a logic console which receives information from a pressure transducer of a sudden decrease in vacuum (increase in pressure) in the pre-pump aspiration conduit. The function of the logic console is to monitor pressure changes within the aspiration conduit as a function of time. Thus, by standard means, the rate of vacuum change within the system can be constantly monitored. Should the rate of vacuum loss exceed a predetermined rate, the logic console would send an electronic signal to the pump which in turn would reverse rotation at a rate and duration which are predetermined and may be programmable, i.e., the rate and/or duration of pump reversal could be proportional to the rate of vacuum loss.

Another mechanism which may be employed to prevent a fluid surge, and which mechanism may be used with or without simultaneous pump reversal, is the following. Upon determining that a sudden decrease of vacuum within the pre-pump aspiration conduit has developed, the logic console sends an electronic signal to an electromechanically operated valve situated at the aspiration conduit at a location which is within or in close proximity to the surgical handpiece. The valve acts to compress or otherwise occlude the aspiration conduit, thus immediately terminating the removal of tissue or fluid from the surgical site. Upon the receipt of electronic information from the pressure transducer that vacuum levels within the aspiration conduit have been reduced to a predetermined level and/or that elimination of the rapid decrease in vacuum within the aspiration conduit by either the aforementioned pump reversal, aspiration conduit obstruction, or by standard venting means have been accomplished, the logic console would deliver an electric signal to the electromechanical system responsible for occlusion of the aspiration conduit, and such obstruction would be relieved by opening of the valve mechanism.

BRIEF DESCRIPTION OF THE DRAWINGS

The nature and advantages of the invention will be better understood when the detailed description of the invention is considered in conjunction with the drawings provided herein.

DETAILED DESCRIPTION OF THE INVENTION AND PREFERRED EMBODIMENTS

The invention will now be described with reference to the preferred embodiments thereof illustrated in FIGS. 1 and 2.

The flow conduit apparatus is adaptable to any surgical instrument which is used to aspirate tissues and/or fluids from the body.

Figure 1:
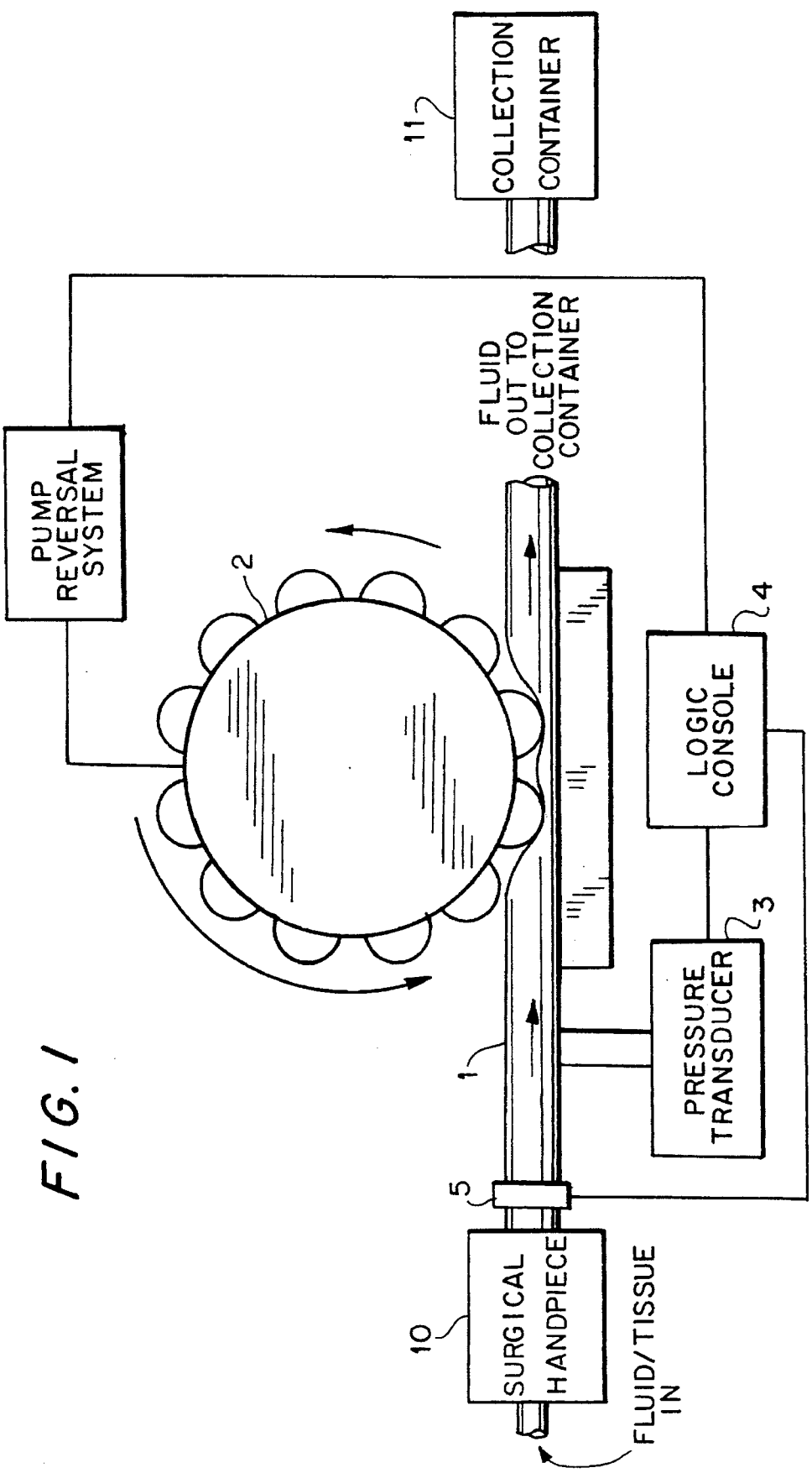
FIG. 1 illustrates schematically a fluid control system comprised of an aspiration conduit 1, which is connected to a collection container, a pump, a pressure transducer, a logic console and an electromechanical valve.

As shown in FIG. 1, fluid and/or material is drawn from the surgical cavity via a surgical handpiece 10 through the aspiration fluid conduit 1 by the pump 2 and is discharged into a collection container 11. A peristaltic pump 2 is preferred, but not required in this invention, because of its lack of contamination, good controllability, and high suction capability. As illustrated in FIG. 1, it stimulates a ferris wheel, rotating and containing sequential protuberances which squeeze the aspiration fluid conduit 1, thereby creating vacuum and flow. Other pumps capable of causing a reversal of fluid flow to occur, such as a scroll pump, may also be used.

A pressure transducer 3 constantly monitors pressure within the aspiration conduit 1, and thereby senses any fluctuations of vacuum, which always occur in the development of a fluid surge within said conduit. The transducer relays such information to the logic console 4 which monitors the rate of pressure change as a function of time. The logic console can be any conventional logic console now available on the market and well known to those skilled in the art. At the moment the rate of vacuum loss reaches or exceeds a pre-determined value, the logic console 4 generates an electric signal which is relayed to the pump 2. The electric signal may be proportional to the rate of change in the vacuum level.

Upon receiving such signal, the pump 2 reverses its rotation, thereby increasing the pressure in the pre-pump aspiration conduit and thus preventing the occurrence of a fluid surge. Also, as a separate function or in conjunction with the above described mechanism, a signal that the rate of vacuum loss has exceeded a predetermined level may be sent from the logic console to an electromechanical control valve 5 situated at or near the surgical handpiece. This valve would then be activated, compressing or otherwise occluding the aspiration conduit. Upon the receipt of electronic information from the pressure transducer that vacuum levels within the aspiration conduit have been reduced to a predetermined level and/or that elimination of the rapid decrease in vacuum within the aspiration conduit by either the aforementioned pump reversal, aspiration conduit obstruction, or by standard venting means have been accomplished, the logic console would deliver an electric signal to the pump 2 which may thereby reverse to its normal rotation and/or to the electromechanical system responsible for occlusion of the aspiration conduit, whereby such obstruction would be relieved by opening of the valve mechanism.

Figure 2:
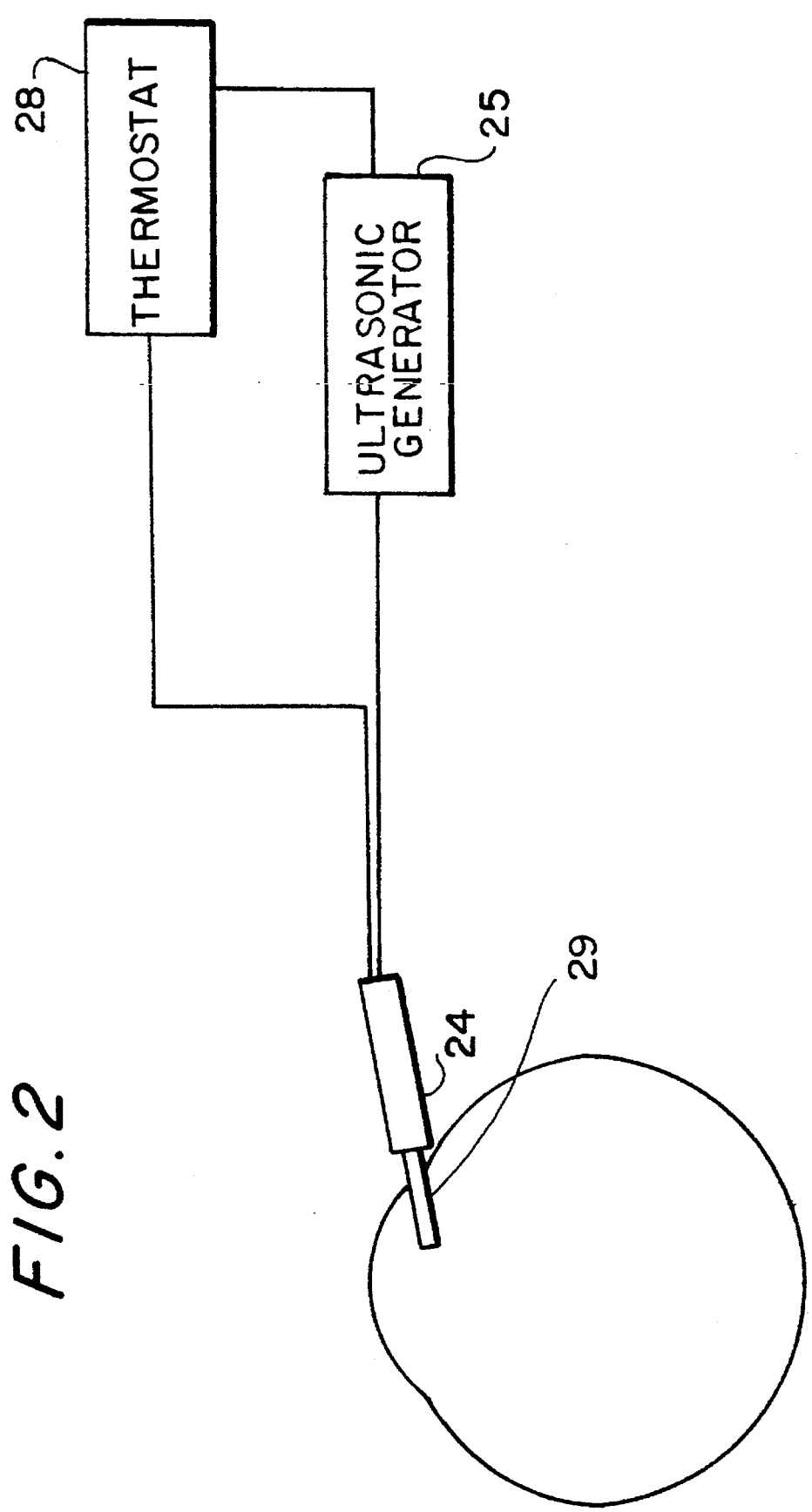
FIG. 2 illustrates schematically a system for removing fluid and/or tissue from a surgical site, the system being comprised of an ultrasonic surgical handpiece, an ultrasonic generator, a thermostat, and a thermocouple.

As illustrated in FIG. 2, the apparatus may be used in conjunction with an ultrasonic surgical handpiece 24, which reduces the material removed from the surgical cavity to a suitable size for aspiration purposes, and an ultrasonic generator 25 for powering the surgical handpiece 24.

In employing an ultrasonic surgical handpiece 24, a thermocouple 29 and a thermostat 28 may be used. The thermocouple 29 will sense the temperature at a selected point of the handpiece, and will relay a signal to the thermostat 28 of such reading. The thermostat 28 will determine when the thermocouple relayed information indicates that the temperature has reached a maximum, predetermined limit. The thermostat will then send a signal to the ultrasonic generator 25 to terminate its power to the surgical handpiece 24, thus preventing the development of a dangerously high temperature at the site, which might otherwise damage the surrounding tissues. The system of FIG. 2 can be used with the system of FIG. 1.

It is accordingly intended that all matter contained in the above description or shown in the accompanying drawings be interpreted as illustrative rather than in a limiting sense.

It is also to be understood that the following claims are intended to cover all of the generic and specific features of the invention as described herein, and all statements of the scope of the invention which, as a matter of language, might be said to fall there between.

Having described the invention, what is claimed as new and secured by Letters Patent is:

1. An apparatus for controlling fluid flow through a surgical instrument in response to sudden release of an obstruction, comprising an aspiration conduit adapted for connection with a surgical instrument;

a pump connected to said aspiration conduit;

a sensor that senses pressure within said aspiration conduit; and a logic console that directs actuation of said pump to pump fluid to flow in one direction through said aspiration conduit to create suction at a pressure level within said aspiration conduit and thereby remove fluid material from the surgical instrument, said logic console making a determination based on the pressure sensed by said sensor as to whether a rate of decrease in vacuum within said aspiration conduit as results from release of an obstruction in said aspiration conduit exceeds an acceptable rate of decrease and, if so, directing said pump to effect reversal in flow direction of the fluid through said aspiration conduit and thereby causing said pressure to increase within said aspiration conduit and prevent the fluid from surging into the aspiration conduit from the surgical instrument and thereafter, in response to making a further determination based on the pressure sensed by said sensor of an occurrence of at least any one of an attainment of an acceptable vacuum level within said aspiration conduit and an elimination of the rate of decrease in vacuum within said aspiration conduit in excess of the acceptable rate of decrease, directing said pump to resume fluid flow in said one direction through said aspiration conduit.

2. An apparatus as in claim 1, wherein said sensor is a pressure transducer, further comprising a logic console that monitors changes in said pressure within said aspiration conduit as a function of time and which provides a signal to said pump to effect said flow reversal in response to monitoring said sudden rise in said pressure.

3. An apparatus as in claim 2, wherein said logic console provides said flow reversal at any one of a rate and a duration which is proportional to a rate of vacuum loss within said aspiration conduit.

4. An apparatus as in claim 1, further comprising a valve occluding said aspiration conduit in response to a rate of vacuum loss within said aspiration conduit exceeding a level.

5. An apparatus as in claim 1 in combination with a surgical instrument handpiece that has a source of power for powering the handpiece; a temperature sensor that senses temperature at an exterior surface of said handpiece; and a thermostat for shutting off said source of power to said handpiece in response to the temperature sensor sensing the temperature as exceeding a level.

6. An apparatus as in claim 5, wherein said temperature sensor is a thermocouple.

7. An apparatus for controlling fluid to a surgical instrument in response to sudden release of an obstruction, comprising an aspiration conduit that removes fluid and material from the surgical instrument;

a valve connected to said actuation conduit and arranged to occlude the same;

a sensor that senses pressure level within said aspiration conduit; and a logic console making a determination as to whether a rate of vacuum decrease within said aspiration conduit as results from release of an obstruction in said aspiration conduit exceeds an acceptable rate of decrease based on pressure levels sensed by said sensor and, if so, directing said valve to actuate to occlude said aspiration conduit and thereafter, in response to making a further determination with the logic console based on the pressure levels sensed by said sensor of an occurrence of at least one of an attainment of an acceptable vacuum level within said aspiration conduit and an elimination of the rate of vacuum loss within said aspiration conduit in excess of the acceptable rate of decrease, directing said valve to actuate to open said aspiration conduit.

8. An apparatus as in claim 7, wherein the surgical instrument includes a handpiece that is powered by a source of power, further comprising a temperature sensor arranged to sense temperature on an exterior surface of the handpiece; and a thermostat responsive to said temperature sensor sensing temperature above a level for shutting off the source of power to said handpiece.

9. An apparatus as in claim 8, wherein said temperature sensor is a thermocouple.

10. A method of controlling fluid to a surgical instrument in response to sudden release of an obstruction, comprising the steps of:

sensing pressure within an aspiration conduit that is adapted for connection with a surgical instrument;

pumping fluid to flow in one direction thorough said aspiration conduit to suction at a pressure level within said aspiration conduit and thereby remove fluid material from the surgical instrument;

effecting reversal in flow direction of the fluid in response to making a determination with a logic console based on the step of sensing that a rate of decline in vacuum level within the aspiration conduit as results from release of an obstruction in the aspiration conduit exceeds an acceptable rate of decrease, said reversal causing said pressure within said aspiration conduit to increase;

thereafter making a determination based on the step of sensing of an occurrence of at least one of attainment of an acceptable vacuum level within said aspiration conduit and an elimination of the rate of decrease in vacuum within the aspiration conduit in excess of said acceptable rate of decrease; and resuming fluid flow in said one direction in response to making the determination of the occurrence having taken place.

11. A method as in claim 10, wherein said flow reversal is carried out at any one of a rate and a duration which is proportional to a rate of vacuum loss within said aspiration conduit.

12. A method as in claim 10, further comprising a valve occluding said aspiration conduit in response to a rate of vacuum loss within said aspiration conduit exceeding a level.

13. A method as in claim 10, further comprising the steps of sensing temperature at an exterior surface of said handpiece while the exterior surface is at a surgical in tissue; and shutting off said source of power to said handpiece in response to sensing the temperature as exceeding a level.

14. A method for controlling fluid flow to a surgical instrument in response to sudden release of an obstruction, comprising the steps of:

removing fluid and material from the surgical instrument;

sensing a pressure level within said aspiration conduit; and occluding the aspiration conduit by closing a valve in response to making a determination with a logic console that a rate of vacuum decrease within said aspiration conduit exceeds an acceptable rate of decrease based on pressure levels sensed by said sensor as results from a release of an obstruction in said aspiration conduit, and, thereafter, opening the aspiration conduit by opening the valve in response to making a further determination with the logic console based on the pressure levels sensed by said sensor of an occurrence of at least one of an attainment of an acceptable vacuum level within said aspiration conduit and an elimination of the rate of vacuum loss within said aspiration conduit in excess of the acceptable rate of decrease.

15. A method as in claim 14, further comprising the steps of:

sensing temperature at an exterior surface of a surgical instrument handpiece while the exterior surface of the handpiece is at a surgical site in tissue; and shutting off a source of power to said handpiece in response to the temperature sensor sensing the temperature as exceeding a level.

* * * * *